(12) United States Patent
Kohls

(10) Patent No.: US 7,643,870 B2
(45) Date of Patent: Jan. 5, 2010

(54) METHOD AND SYSTEM OR MANAGING ECGS IN A CLINICAL TRIAL

(75) Inventor: Mark Kohls, New Berlin, WI (US)

(73) Assignee: The General Electric Company, Schenectady, NY (US)

( * ) Notice: Subject to any disclaimer, the term of this patent is extended or adjusted under 35 U.S.C. 154(b) by 348 days.

(21) Appl. No.: 11/619,056

(22) Filed: Jan. 2, 2007

(65) Prior Publication Data

US 2008/0161704 A1 Jul. 3, 2008

(51) Int. Cl.
*A61B 5/0402* (2006.01)
(52) U.S. Cl. ..................................... 600/509
(58) Field of Classification Search .......... 600/508–523
See application file for complete search history.

(56) References Cited

U.S. PATENT DOCUMENTS

| | | | |
|---|---|---|---|
| 6,708,057 B2 * | 3/2004 | Morganroth | 600/509 |
| 6,847,840 B2 | 1/2005 | DePasquale et al. | |
| 2004/0044292 A1 * | 3/2004 | Yasushi et al. | 600/509 |
| 2004/0152056 A1 | 8/2004 | Lamb et al. | |
| 2004/0171955 A1 | 9/2004 | Morganroth | |
| 2008/0132799 A1 * | 6/2008 | Xue | 600/509 |

OTHER PUBLICATIONS

International Conference on Harmonisation of Technical Requirements for Registration of Pharmaceuticals for Human Use, (May 2005) "ICH Harmoniseed Tripartite Guidelines: The Clinical Evaluation of QT/QTc Interval Prolongation and Proarrhythmic Potential for Non-Antiarrhythmic Drugs,".
FDA, DIA and Heart Rhythm Society (Apr. 2005) "The Use of ECGs in Clinical Trials: A Public Discussion of the Proposed ICH E14 Regulatory Guidance," Bethesda North Marriott, MD.
American Society of Health-System Pharmacists (Jan. 2006) "Medline Plus Drug Information: Moxifloxacin" Webpage printout.
Shah, RR (2005) "Drugs, QT Interval Prolongation and ICH E14: the need to get it right," Medscape from WebMD.

* cited by examiner

*Primary Examiner*—Scott M Getzow
(74) *Attorney, Agent, or Firm*—Andrus, Sceales, Starke & Sawall, LLP

(57) ABSTRACT

The present disclosure includes a method and system for managing ECGs in a clinical trial including a processor, storage media, ECG acquisition system, user interface device, and the appropriate databases configured to collect and store a set of trial specific drug ECG recordings. The system and method allows a trial administrator to select a set of placebo ECG recordings and a set of known QT prolonged ECG recordings from databases and adjust these sets according to the parameters of the study. Interpretations are made on this superset of ECG recordings and the interpretation is outputted to a user.

17 Claims, 2 Drawing Sheets

METHOD AND SYSTEM OR MANAGING ECGS IN A CLINICAL TRIAL

FIELD OF THE DISCLOSURE

The present disclosure relates to the field of diagnostic cardiology, specifically managing ECGs acquired in a clinical trial.

BACKGROUND OF THE DISCLOSURE

New drugs follow a rigorous process from compound discovery to final approval requiring many years and many millions of dollars of investment. In recent years, the concept of the Thorough QT Study (TQT) has been developed by the International Committee on Harmonization (ICH) in their E14 Guidance document (E14). This study is done, as the name implies, to develop a thorough and a complete as possible understanding of the effects of the new compound on ventricular repolarization. In a typical TQT study, three sets of ECGs are collected. The three sets of ECGs are: patients on a placebo; patients on a known QT prolonging drug, typically Moxifloxacin, a fluoroquinolone antibiotic, with well understood QT prolonging properties, this is known as the "positive control"; and patients receiving the new drug being tested. The positive control drug can be any drug with well-known QT prolonging effects.

The total number of ECGs collected varies based on study design, but 15,000-18,000 ECGs is the generally accepted number in industry. While it is somewhat obvious that a trial would contain patients on the new compound as well as placebo, the reason for the patients on the known QT Prolonging drug is somewhat obscure. These patients are included in the trial so that when the ECGs are overread by clinician(s), it can be shown that the overreader(s) were capable of detecting the QT prolongation that is typically caused by the drug. In other words, if they did not detect the prolongation in the positive control the overreading process would be invalidated.

The cost of a TQT study is generally estimated to be between $500K and $1M dollars and involves recruiting perhaps 20-30 healthy volunteers to participate. While the group that receives Moxifloxacin is at little risk from taking the drug, they are not at zero risk of complications. Administering any drug to a healthy person that does not actually need to take it involves risks of severe allergic reaction, anaphylactic shock, arrhythmia, etc. While Moxifloxacin is generally well tolerated by patients, the drug labeling includes possible side effects such as: upset stomach; diarrhea; dizziness; headache; stomach pain; and vomiting. Numerous other side effects are also mentioned, including causing QT prolongation, of course. It would be desirable to create a system that allowed for the positive control group to be eliminated from future clinical trials while still meeting the need of having a positive control set of ECG recordings in the trial specific data set to be reviewed.

SUMMARY OF THE DISCLOSURE

The present disclosure includes a method and system for managing ECGs in a clinical trial including a processor, storage media, ECG acquisition system, user interface device, and the appropriate databases configured to collect and store a set of trial specific drug ECG recordings. The system and method allows a trial administrator to select a set of placebo ECG recordings and a set of known QT prolonged ECG recordings from databases and adjust these sets according to the parameters of the study. Interpretations are made on this superset of ECG recordings and the interpretation is outputted to a user.

One aspect of the present disclosure is a method of managing an ECG clinical trial, the method comprises collecting a set of trial specific drug ECG recordings from a patient, selecting a set of placebo ECG recordings and a set of known QT prolonged ECG recordings, making an interpretation based on an analysis of the set of trial specific drug ECG recordings, the set of placebo ECG recordings and the set of known QT prolonged ECG recordings, and outputting the interpretation to a user. The method further comprises storing the set of trial specific drug ECG recordings in a trial specific drug ECG database and retrieving the set of trial specific drug ECG recordings form the trial specific drug ECG database before making the interpretation wherein the set of placebo ECG recordings are selected from a placebo ECG database. The set of known QT prolonged ECG recordings in this method are selected from a known QT prolonged ECG database and the step of selecting the set of known QT prolonged ECG recordings further includes sorting a collection of known QT prolonged ECG recordings according to a T-wave state, adjusting the set of placebo ECG recordings and the set of known QT prolonged ECG recordings based on a predetermined set of study parameters. The set of known QT prolonged ECG recordings in this method are based on a response to Moxifloxacin, and maintaining a log of the selected set of placebo ECG recordings and the selected set of known QT prolonged ECG recordings wherein the selecting step and the step of making the interpretation are made using a user interface device.

Another aspect of the present disclosure is a system for managing an ECG trial, the system comprises an ECG acquisition device configured to collect a set of trial specific drug ECG recordings from a patient, a placebo ECG database configured to store placebo ECG database recordings, the placebo ECG database further configured such that a user can select a set of placebo ECG recordings, a known QT prolonged ECG database configured to store known QT prolonged ECG recordings, the known QT prolonged database further configured such that a user can select a set of known QT prolonged ECG recordings, wherein a reader makes an interpretation based on an analysis of the set of trial specific drug ECG recordings, the set of placebo ECG recordings, and the known QT prolonged ECG recordings, and a user interface device configured to receive the interpretation from the reader. The system further comprises a trial specific database configured to store the set of trial specific drug ECG recordings wherein the set of trial specific drug ECG recordings are retrieved form the trial specific drug ECG database before the interpretation is made, wherein the known QT prolonged ECG database is configured to sort the known QT prolonged ECG recordings according to a T-wave state and the set of placebo ECG recordings and the set of known QT prolonged ECG recordings are adjusted based on a predetermined set of study parameters. The set of known QT prolonged ECG recordings in the system are based on a response to Moxifloxacin and may further comprise maintaining a log of the selected set of placebo ECG recordings and the selected set of known QT prolonged ECG recordings. The system further wherein the set of placebo ECG recordings and the set of known QT prolonged ECG recordings may be adjusted to any of the parameters: subject ID number; recording date; recording time; visit number; recording device serial number; location; and study.

Yet another aspect of the present disclosure is a system for managing an ECG clinical trial, the system comprises an ECG acquisition system configured to collect a set of trial specific drug recordings from a patient, a storage media for storing a computer application, a processor coupled to an ECG acquisition system and the storage media, and configured to execute the computer application, wherein when the computer application is executed a set of placebo ECG recordings and a set of known QT prolonged ECG recordings are selected, the set of placebo ECG recordings and the set of known QT prolonged ECG recordings are adjusted based on a predetermined set of study parameters, an interpretation is made based on an analysis of the set of trial specific drug ECG recordings, the set of placebo ECG recordings and the set of known QT prolonged ECG recordings, and the interpretation is outputted to a user.

DETAILED DESCRIPTION

The system and method of the disclosure includes a database of ECG recordings recorded from patients on placebo and on known QT prolonging drugs, for example Moxifloxcin, and tools for reviewing ECGs on screen from a clinical trial. In the system and method, a trial administrator selects individual or sets of previous recordings for inclusion in a study. The administrator selects the number of recordings per patient and number of patients to match the study design and criteria. The administrator then adjusts the following demographic parameters: subject ID number; recording dates and times; visit number; recording device serial number; location; and study information. It should be noted that this is not a complete list of parameters, and a system according to the present disclosure may be tailored to include more or fewer parameters.

Adjusting these parameters allows the study administrator who is not involved in the overreading process to create a placebo and positive control set of ECG recordings that are demographically indistinguishable from those acquired from patients actually "on drug." The size of the placebo and positive control sets would be indistinguishable from the acquired data sets as well.

The database is of sufficient size that the overreaders are not able to recognize the same ECG recordings over time. The system also maintains a log of which recordings were used previously. The system has the capability to review ECG measurements across studies of the same ECG recordings.

Figure 1:
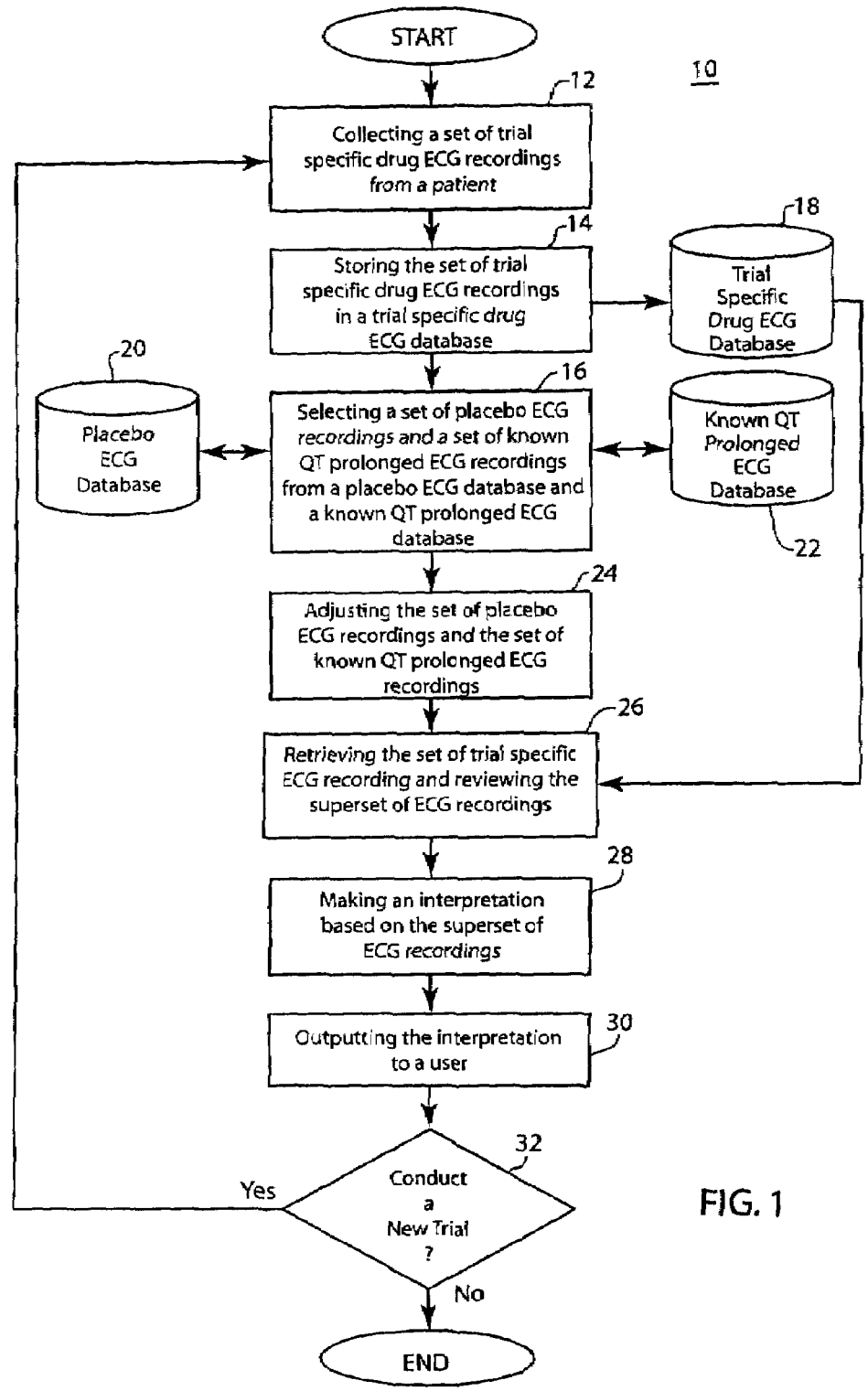
FIG. 1 illustrates a flow chart according to an embodiment of the present method.

Referring to FIG. 1, a managing method 10 of the present disclosure is depicted. In step 12, a set of trial specific drug ECG recordings are collected from a patient. In step 14, the collected set of trial specific ECG recordings is stored in the trial specific drug ECG database 18. In step 16, a set of placebo ECG recordings and a set of known QT prolonged ECG recordings are selected from a placebo ECG database 20 and a known QT prolonged ECG database 22. The set of placebo ECG recordings in the placebo ECG database 20 are placebo ECG recordings that have been collected previously, such as in previous TQT studies. Likewise, the known QT prolonged database 22 includes ECG data from patients in previous studies who where given drugs that are known to prolong a patient's QT profile. The set of known prolonged QT ECG recordings and the set of placebo ECG records are preferably collected by an administrator of the TQT study. As described above, this administrator may select the number of recordings per patient and the number of patients to match the study design and criteria. The administrator may also adjust the demographic parameters as listed above. This selection step creates a placebo and positive control set that are demographically indistinguishable from the collected and stored set of trial specific drug ECG recordings from steps 12 and 14, and stored in the trial specific drug ECG database 18.

Referring back to the managing method 10 of FIG. 1, in step 24, the set of placebo ECG recordings and the set of known QT prolonged ECG recordings are adjusted. Referring back to the previous paragraph, these sets of recording are adjusted according to demographic parameters such as, but not limited to identification number, recording dates and times, visit numbers, recording device serial numbers, location, and study information. It is also contemplated that in step 16, the known QT prolonged ECG database 22 includes the ability for an administrator to sort the known QT prolonged ECGs in the database 22 according to the types of T-wave shapes attributed to each of the known QT prolonged ECGs. This allows the administrator to select ECGs with T-wave shapes indicative of specific T-wave abnormalities commonly associated with QT prolongation. The administrator may be able to sort the known QT prolonged ECGs in the database 22 according to a number of known T-wave shapes such as, but not limited to, inverted T-waves, notched T-waves, flat T-waves, T-waves with an inverted U-wave, and alternans patterns T-wave, noisy T-waves and any other T-waves known in the art or discovered in the art at a later time.

In step 26, the set of trial specific ECG recording is retrieved from the trial specific drug ECG database 18 and the super set of ECG recordings is then reviewed. The super set of ECG recordings includes the set of placebo ECG recordings, the set of known QT prolonged ECG recordings, and the trial specific ECG database. Preferably, the super set of ECG recordings is reviewed by study overreaders, who are usually specially trained personnel. In step 28, an interpretation is made based on the superset of ECG recordings. This interpretation is preferably made by the study overreaders, based on their review of the superset of ECG recordings. In step 30, the interpretation of the super set of ECG recordings is preferably outputted to a user interface device for review by the study administrator. Here, the study administrator may process the interpretation and organize it such that the results of the study may be clearly displayed and reviewed. Lastly, in step 32, if a new trial is to be conducted the managing method 10 returns to step 12 where a new set of trial specific drug ECG recordings is collected. If in step 32 no new trial is to be conducted, then the managing method 10 ends.

Figure 2:
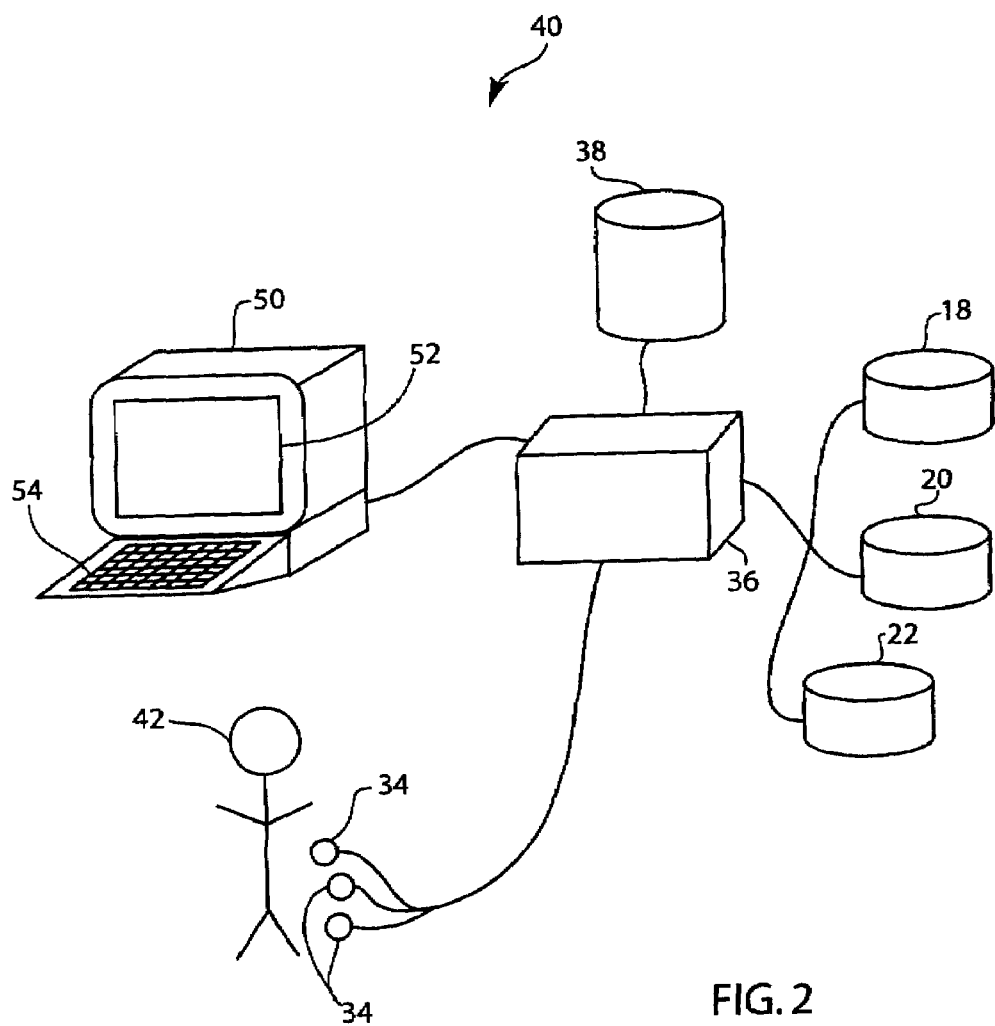
FIG. 2 illustrates a block diagram according to an embodiment of the present system.

FIG. 2 depicts a block diagram of an embodiment of the detection system 40. Here, an ECG acquisition system 34 known in the art, is attached to a patient 42 and a set of ECG data is acquired from the patient 42. A computer software application is stored in a storage media 38, and executed on a processor 36. When executed, the computer software application effectuates the method as described above. It has been contemplated that the detection system 40 as depicted and described may include or may be implemented within an existing hospital ECG management system, or may even stand-alone. Still referring to FIG. 2, the acquired ECG data from the patient 42 is stored in the trial specific drug ECG database 18. A study administrator, utilizing the user interface device 50, to select a set of placebo ECG recordings from the placebo ECG database 20, and a set a set of known QT prolonged ECG recordings from the known QT prolonged ECG database 22. The administrator interfaces with the user interface device 50 with an input device 54 and a graphical user interface 52. Still referring to FIG. 2, the system administrator may adjust the set of placebo ECG recordings and the set of known QT prolonged ECG recordings using the user interface device 50, and then retrieves the set of trial specific ECG recordings form the trial specific drug ECG database.

Still referring to FIG. 2, at least one study overreader (not shown) is responsible for reviewing the superset of ECG recordings, including the trial specific drug ECG recordings, the placebo ECG recordings and the know QT prolonged ECG recordings. The overreaders review this super set using preferably using similar user interface devices 50 as used by the study administrator. As noted previously, while the study administrator is able to see which recordings are trial specific drug recordings, or placebo recordings, or known QT prolonged recordings, the overreaders are not made privy to this information, and overread all of the recordings as one super set. The overreaders then make an interpretation based on their review of the superset of ECG recordings and output the interpretation back to the study administrator of the user interface device 50.

The user interface device 50 may also include a printer (not shown) or other output device for outputting the interpretation to the administrator, a physician or other system user. The input device 54 and GUI 52 allow a user to view the interpretation and other ECG results on the screen of a user interface device 50 such as a terminal (as shown), or alternative user interface devices 50 such as PDAs, medical monitors, or any other known user interface devices 50 in the art. Still referring to FIG. 2, the detection system 40, executing the computer software application, is configured to save the interpretation to the storage media and also to log which placebo recordings and known QT prolongation recordings have been used, when, and how many times.

The system and method as described has significant advantages over the prior art. The system and method eliminates the need to repeatedly expose healthy patients to a drug to create a positive control for a clinical trial. The system and method also eliminates the need to record ECGs from placebo patients. In addition, the recordings are used to train overreaders and test their ability to properly measure and detect the relevant QT interval signal.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of managing an ECG clinical trial, the method comprising:
    collecting a set of trial specific drug ECG recordings from a patient;
    selecting a set of placebo ECG recordings and a set of known QT prolonged ECG recordings;
    adjusting the set of placebo ECG recordings and the set of known QT prolonged ECG recordings based on a predetermined set of demographic study parameters;
    making an interpretation based on an analysis of the set of trial specific drug ECG recordings, the set of placebo ECG recordings and the set of known QT prolonged ECG recordings; and
    outputting the interpretation to a user.

2. The method as claimed in claim 1, further comprising storing the set of trial specific drug ECG recordings in a trial specific drug ECG database.

3. The method as claimed in claim 2, further comprising retrieving the set of trial specific drug ECG recordings form the trial specific drug ECG database before making the interpretation.

4. The method as claimed in claim 1, wherein the set of placebo ECG recordings are selected from a placebo ECG database.

5. The method as claimed in claim 1, wherein the set of known QT prolonged ECG recordings are selected from a known QT prolonged ECG database.

6. The method as claimed in claim 1, wherein the step of selecting the set of known QT prolonged ECG recordings further includes sorting a collection of known QT prolonged ECG recordings according to a T-wave state.

7. The method as claimed in claim 1, wherein the set of known QT prolonged ECG recordings are based on a response to Moxifloxacin.

8. The method of claim 1, further comprising maintaining a log of the selected set of placebo ECG recordings and the selected set of known QT prolonged ECG recordings.

9. The method as claimed in claim 1, wherein the selecting step and the step of making the interpretation are made using a user interface device.

10. A system for managing an ECG trial, the system comprising:
    an ECG acquisition device configured to collect a set of trial specific drug ECG recordings from a patient;
    a placebo ECG database configured to store placebo ECG database recordings, the placebo ECG database further configured such that a user can select a set of placebo ECG recordings;
    a known QT prolonged ECG database configured to store known QT prolonged ECG recordings, the known QT prolonged database further configured such that a user can select a set of known QT prolonged ECG recordings, wherein the set of placebo ECG recordings and the set of known QT prolonged ECG recordings are adjusted based on a predetermined set of demographic study parameters, and further wherein a reader makes an interpretation based on an analysis of the set of trial specific drug ECG recordings, the set of placebo ECG recordings, and the known QT prolonged ECG recordings; and
    a user interface device configured to receive the interpretation from the reader.

11. The system as claimed in claim 10, further comprising a trial specific database configured to store the set of trial specific drug ECG recordings.

12. The system as claimed in claim 11, wherein the set of trial specific drug ECG recordings are retrieved form the trial specific drug ECG database before the interpretation is made.

13. The system as claimed in claim 10, wherein the known QT prolonged ECG database is configured to sort the known QT prolonged ECG recordings according to a T-wave state.

14. The system as claimed in claim 10, wherein the set of known QT prolonged ECG recordings are based on a response to Moxifloxacin.

15. The system as claimed in claim 10, further comprising maintaining a log of the selected set of placebo ECG recordings and the selected set of known QT prolonged ECG recordings.

16. The system as claimed in claim 10, wherein the set of placebo ECG recordings and the set of known QT prolonged ECG recordings may be adjusted to any of the parameters:

subject ID number; recording date; recording time; visit number; recording device serial number; location; and study.

17. A system for managing an ECG clinical trial, the system comprising:
- an ECG acquisition system configured to collect a set of trial specific drug recordings from a patient;
- a storage media storing a computer application;
- a processor coupled to an ECG acquisition system and the storage media, and configured to execute the computer application, wherein when the computer application is executed a set of placebo ECG recordings and a set of known QT prolonged ECG recordings are selected, the set of placebo ECG recordings and the set of known QT prolonged ECG recordings are adjusted based on a predetermined set of demographic study parameters, an interpretation is made based on an analysis of the set of trial specific drug ECG recordings, the set of placebo ECG recordings and the set of known QT prolonged ECG recordings, and the interpretation is outputted to a user.

* * * * *

UNITED STATES PATENT AND TRADEMARK OFFICE
CERTIFICATE OF CORRECTION

PATENT NO. : 7,643,870 B2 Page 1 of 1
APPLICATION NO. : 11/619056
DATED : January 5, 2010
INVENTOR(S) : Mark Kohls It is certified that error appears in the above-identified patent and that said Letters Patent is hereby corrected as shown below:

Title Pg, Item (54) Title should read as follows:

--METHOD AND SYSTEM FOR MANAGING ECGS IN A CLINICAL TRIAL--

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,643,870 B2
APPLICATION NO. : 11/619056
DATED : January 5, 2010
INVENTOR(S) : Mark Kohls Page 1 of 1

It is certified that error appears in the above-identified patent and that said Letters Patent is hereby corrected as shown below:

Title Pg, Item (54) and at Column 1, lines 1 and 2, Title should read as follows:

--METHOD AND SYSTEM FOR MANAGING ECGS IN A CLINICAL TRIAL--

This certificate supersedes the Certificate of Correction issued February 23, 2010.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,643,870 B2 | Page 1 of 1 |
| APPLICATION NO. | : 11/619056 | |
| DATED | : January 5, 2010 | |
| INVENTOR(S) | : Mark Kohls | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this

Sixteenth Day of November, 2010

David J. Kappos
*Director of the United States Patent and Trademark Office*